(12) United States Patent
Pelissier et al.

(10) Patent No.: US 10,405,829 B2
(45) Date of Patent: Sep. 10, 2019

(54) ULTRASOUND MACHINE HAVING SCALABLE RECEIVE BEAMFORMER ARCHITECTURE COMPRISING MULTIPLE BEAMFORMERS WITH COMMON COEFFICIENT GENERATOR AND RELATED METHODS

(71) Applicant: Clarius Mobile Health Corp., Vancouver (CA)

(72) Inventors: Laurent Pelissier, North Vancouver (CA); Kwun-Keat Chan, Vancouver (CA); Trevor Hansen, Vancouver (CA)

(73) Assignee: Clarius Mobile Health Corp., Brunaby, British Columbia (CA)

( * ) Notice: Subject to any disclaimer, the term of this patent is extended or adjusted under 35 U.S.C. 154(b) by 1058 days.

(21) Appl. No.: 14/556,999

(22) Filed: Dec. 1, 2014

(65) Prior Publication Data

US 2016/0151045 A1   Jun. 2, 2016

(51) Int. Cl.
*A61B 8/00*   (2006.01)
*A61B 8/14*   (2006.01)
(Continued)

(52) U.S. Cl.
CPC .............. *A61B 8/4483* (2013.01); *A61B 8/14* (2013.01); *A61B 8/4427* (2013.01); *A61B 8/461* (2013.01);
(Continued)

(58) Field of Classification Search
CPC combination set(s) only.
See application file for complete search history.

(56) References Cited

U.S. PATENT DOCUMENTS

| 4,136,325 A | 1/1979 | Takamizawa et al. |
| 4,170,766 A | 10/1979 | Pridham et al. |

(Continued)

FOREIGN PATENT DOCUMENTS

| AU | 2012319035 B2 | 4/2013 |
| AU | 2013219177 A1 | 3/2014 |

(Continued)

OTHER PUBLICATIONS

Kim, G.-D. et al., "A Single FPGA-Based Portable Ultrasound Imaging System for Point-of-Care Applications", IEEE Transactions on Ultrasonics, Ferroelectrics, and Frequency Control 59(7): 1386-1394 (Jul. 2012).

(Continued)

*Primary Examiner* — Carolyn A Pehlke
(74) *Attorney, Agent, or Firm* — Julian Ho (57) ABSTRACT

An apparatus and method for generating high quality, high frame rate images in a handheld or hand-carried ultrasound imaging machine. The apparatus includes a time-multiplexed beamformer coefficient generator that supplies the necessary delay and weight coefficients to process multiple beams in parallel via a beamforming coefficient bus. This approach reduces the required hardware and power consumption to satisfy the physical space and power requirements of a handheld probe. To improve image quality, the ultrasound machine may optionally use synthetic aperture to improve penetration and resolution. The ultrasound machine may also use pulse inversion harmonics to improve image quality by improving signal-to-noise ratio.

32 Claims, 5 Drawing Sheets

(51) Int. Cl.

| | | |
|---|---|---|
| *A61B 8/08* | (2006.01) | |
| *G01S 7/524* | (2006.01) | |
| *G10K 11/34* | (2006.01) | |
| *G01S 7/52* | (2006.01) | |
| *G01S 15/89* | (2006.01) | |

(52) U.S. Cl.
CPC ............ *A61B 8/5207* (2013.01); *G01S 7/524* (2013.01); *G01S 7/52046* (2013.01); *G01S 15/8988* (2013.01); *G10K 11/346* (2013.01); *G10K 11/348* (2013.01); *G01S 15/8963* (2013.01)

(56) References Cited

U.S. PATENT DOCUMENTS

| | | | |
|---|---|---|---|
| 4,173,007 A | 10/1979 | McKeighen et al. | |
| 4,267,584 A | 5/1981 | McKeighen et al. | |
| 4,401,957 A | 8/1983 | McKeighen et al. | |
| 4,542,653 A | 9/1985 | Liu | |
| 4,787,392 A | 11/1988 | Saugeon | |
| 5,111,695 A | 5/1992 | Engeler et al. | |
| 5,230,340 A | 7/1993 | Rhyne | |
| 5,345,426 A | 9/1994 | Lipschutz | |
| 5,369,624 A | 11/1994 | Fukukita et al. | |
| 5,388,461 A | 2/1995 | Rigby | |
| 5,465,722 A | 11/1995 | Fort et al. | |
| 5,469,851 A * | 11/1995 | Lipschutz | G01N 29/069 600/447 |
| 5,501,219 A | 3/1996 | Phelps et al. | |
| 5,522,391 A | 6/1996 | Beaudin et al. | |
| 5,544,128 A | 8/1996 | Kim et al. | |
| 5,573,001 A * | 11/1996 | Petrofsky | G01S 7/52026 600/447 |
| 5,581,036 A | 12/1996 | Chang et al. | |
| 5,581,517 A | 12/1996 | Gee et al. | |
| 5,596,550 A | 1/1997 | Rowe, Jr. et al. | |
| 5,627,799 A | 5/1997 | Hoshuyama | |
| 5,653,236 A | 8/1997 | Miller | |
| 5,685,308 A | 11/1997 | Wright et al. | |
| 5,690,114 A | 11/1997 | Chiang et al. | |
| 5,722,412 A | 3/1998 | Pflugrath et al. | |
| 5,817,024 A | 10/1998 | Ogle et al. | |
| 5,827,188 A | 10/1998 | Wright et al. | |
| 5,836,881 A | 11/1998 | Bae | |
| 5,844,139 A | 12/1998 | Miller et al. | |
| 5,882,307 A | 3/1999 | Wright et al. | |
| 5,893,363 A | 4/1999 | Little et al. | |
| 5,905,692 A | 5/1999 | Dolazza et al. | |
| 5,997,479 A | 12/1999 | Savord et al. | |
| 6,042,547 A | 3/2000 | Wright et al. | |
| 6,110,116 A | 8/2000 | Wright et al. | |
| 6,123,671 A | 9/2000 | Miller | |
| 6,494,842 B2 * | 12/2002 | Bae | G01S 7/52034 600/447 |
| 6,671,227 B2 | 12/2003 | Gilbert et al. | |
| 6,695,783 B2 | 2/2004 | Henderson et al. | |
| 6,780,154 B2 | 8/2004 | Hunt et al. | |
| 6,885,338 B2 | 4/2005 | Gaus, Jr. et al. | |
| 7,500,952 B1 | 3/2009 | Chiang et al. | |
| 7,508,737 B1 | 3/2009 | Alexandru | |
| 7,540,842 B2 | 6/2009 | Napolitano et al. | |
| 7,920,440 B2 | 4/2011 | Jiang et al. | |
| 7,925,504 B2 | 4/2011 | Tsujikawa | |
| 8,002,708 B2 | 8/2011 | Shah et al. | |
| 8,088,068 B2 | 1/2012 | Yao et al. | |
| 8,211,018 B2 | 7/2012 | Kang et al. | |
| 8,428,378 B2 | 4/2013 | Mansour | |
| 8,535,227 B2 | 9/2013 | Halmann et al. | |
| 8,672,850 B1 | 3/2014 | Miller | |
| 8,690,782 B2 | 4/2014 | Colby | |
| 8,743,914 B1 | 6/2014 | Jensen | |

| | | | |
|---|---|---|---|
| 2002/0171580 A1 | 11/2002 | Gaus, Jr. et al. | |
| 2005/0288588 A1* | 12/2005 | Weber | A61B 8/483 600/447 |
| 2006/0058655 A1 | 3/2006 | Little | |
| 2008/0009725 A1 | 1/2008 | Bae et al. | |
| 2008/0154592 A1 | 6/2008 | Tsujikawa | |
| 2008/0262351 A1 | 10/2008 | Scampini | |
| 2011/0077522 A1 | 3/2011 | Sato | |
| 2011/0222791 A1 | 9/2011 | Mansour | |
| 2011/0237950 A1* | 9/2011 | Meng | A61B 8/14 600/447 |
| 2012/0053460 A1 | 3/2012 | Blalock et al. | |
| 2012/0281902 A1 | 11/2012 | Oikawa et al. | |
| 2014/0058262 A1 | 2/2014 | Yoda | |
| 2014/0058270 A1 | 2/2014 | Davidsen et al. | |
| 2014/0064514 A1 | 3/2014 | Mikami et al. | |
| 2014/0071221 A1 | 3/2014 | Dave et al. | |
| 2014/0071789 A1 | 3/2014 | Brodsky et al. | |
| 2014/0073340 A1 | 3/2014 | Nilsson et al. | |
| 2014/0073923 A1 | 3/2014 | Haugaard et al. | |
| 2014/0080420 A1 | 3/2014 | Yang et al. | |
| 2014/0086354 A1 | 3/2014 | Kludt et al. | |
| 2014/0091968 A1 | 4/2014 | Harel et al. | |
| 2014/0105416 A1 | 4/2014 | Huttunen et al. | |
| 2014/0112487 A1 | 4/2014 | Laska et al. | |
| 2014/0114190 A1 | 4/2014 | Chiang et al. | |
| 2014/0119301 A1 | 5/2014 | Park et al. | |
| 2014/0121521 A1 | 5/2014 | Poland et al. | |
| 2014/0121524 A1* | 5/2014 | Chiang | A61B 8/5207 600/459 |
| 2014/0126323 A1 | 5/2014 | Li et al. | |
| 2014/0145880 A1 | 5/2014 | Stahlberg et al. | |
| 2014/0161272 A1 | 6/2014 | Marquis et al. | |

FOREIGN PATENT DOCUMENTS

| | | |
|---|---|---|
| EP | 0260353 B1 | 9/1990 |
| EP | 0696792 A2 | 2/1996 |
| EP | 0782126 B1 | 6/2003 |

OTHER PUBLICATIONS

Jensen, J.A. et al., "Synthetic aperture ultrasound imaging", Ultrasonics, 44, Supplement(0), e5-e15 (Aug. 2006).

Luo, J. et al., "Compact Beamformer Design with High Frame Rate for Ultrasound Imaging", Sensors & Transducers, vol. 168, Issue 4, pp. 237-242 (Apr. 2014).

Shattuck, D.P. et al., "Explososcan: A parallel processing technique for high speed ultrasound imaging with linear phased arrays", J. Acoust. Soc. Am. 75(4): 1273-1282 (Apr. 1984).

Smith, S.W. et al., "High-Speed Ultrasound Volumetric Imaging System—Part I: Transducer Design and Beam Steering", IEEE Transactions on Ultrasonics, Ferroelectrics and Frequency Control 38(2), 100-108 (Mar. 1991).

Steinberg, B.D., "Digital Beamforming in Ultrasound", IEEE Transactions on Ultrasonics, Ferroelectrics and Frequency Control 39(6): 716-721 (Nov. 1992).

Haynes, T., "A Primer on Digital Beamforming", Spectrum Signal Processing (Mar. 1998).

Cephasonics, Inc., "32/64-channel Embedded-Ultrasound Platform", cQuest Dragonfly Preliminary Product Brief (2013) Rev. 1.8.

Thiele, K. et al., "Exploring nSIGHT Imaging—a totally new architecture for premium ultrasound", Philips EPIQ Ultrasound System, Koninklijke Philips N.V., Jun. 2013.

Abstract of Hergum, T. et al., "Parallel Beamforming using Synthetic Transmit Beams", published in IEEE Transactions on Ultrasonics, Ferroelectrics and Frequency Control (2007) 54.2: 271-280; available at http://ieeexplore.ieee.org/abstract/document/4107686/, last accessed Feb. 16, 2017.

Thomenius, K.E., "Evolution of Ultrasound Beamformers", Proceedings of the IEEE Ultrasonics Symposium (1996) 2: 1615-1622.

* cited by examiner

ULTRASOUND MACHINE HAVING SCALABLE RECEIVE BEAMFORMER ARCHITECTURE COMPRISING MULTIPLE BEAMFORMERS WITH COMMON COEFFICIENT GENERATOR AND RELATED METHODS

FIELD

This invention generally relates to ultrasound imaging machines which form ultrasonic beams by time delay and summation of return signals in a multiplicity of parallel channels. In particular, the invention relates to systems and methods for providing the required beamforming delays for channel processing in a scalable architecture. In some embodiments the systems and methods are implemented in handheld or hand-carried devices.

BACKGROUND

Ultrasound imaging machines are an important tool for diagnosis and therapy in a wide range of medical applications. Historically, ultrasound machines were large, expensive units used only in radiology departments by highly trained specialists. To increase portability and enable ultrasound to be used at the point-of-care and by more users, various attempts have been made to reduce the size and cost of these systems. However, handheld or hand-carried devices are generally constrained in terms of the available power and space. To address these constraints, compromises are often made on the electronics. Such compromises tend to reduce temporal or spatial resolution, which, in turn, negatively affect image quality.

An ultrasound image is typically composed of multiple scanlines. A single scanline (or small localized group of scanlines) is acquired by transmitting ultrasound energy focused at a point in the region of interest, and then receiving reflected energy over time. The focused transmit energy is referred to as a transmit beam. A scanline can be parameterized using a start position and an angle. During the time after transmit, one or more receive beamformers coherently sum the energy received by different channels, with dynamically changing delays (or phase rotations), to produce peak sensitivity along the desired scanlines at ranges proportional to the elapsed time. Conventionally, beamforming delay values are pre-calculated and stored in memory. The resulting focused sensitivity pattern is referred to as a receive beam. The resolution of a scanline is a result of the directivity of the associated transmit and receive beam pair.

Ultrasound transducers typically comprise arrays of small piezoelectric elements. In some cases, a subset of the elements in an array are used to transmit or receive an ultrasound beam. Such subsets are respectively called transmit or receive "apertures". Image quality can be improved by using a larger aperture.

A common method for reducing power consumption and circuit size is to reduce the number of front-end components such as analog-to-digital converters (ADCs) and amplifiers. However, fewer channels limits the maximum size of the receive aperture. This can undesirably result in reduced penetration and resolution of the ultrasound images.

A common method for improving image quality with fewer receive channels is to use a synthetic aperture. A synthetic aperture can be achieved by combining different sets of echoes from multiple similar transmit events. This yields a larger effective aperture which improves penetration and resolution. However, since a synthetic aperture requires multiple similar transmit events, it takes longer to acquire the data required to form each image. This can result in an undesirable decrease in frame rate.

Another method for improving image quality is pulse inversion harmonic imaging, also known as phase inversion imaging. This imaging method relies on the detection of harmonic echoes. Two pulses of similar amplitude but inverted phase are transmitted in close temporal succession. The resulting received signals are then combined, which causes linear scattering to cancel out, thus improving signal-to-noise ratio. Again, since multiple similar transmit events are required, this method also reduces the frame rate.

Frame rate can be improved by processing multiple receive beams for each transmit event. One way to process multiple beams in parallel is to provide multiple sets of beamformer hardware. Not only is this additional hardware expensive, but it is neither practical nor efficient in a portable system where physical space and power are limited. Furthermore, as the number of beamformers grows, the storage size required for pre-calculated beamforming coefficients grows as well, so that the number of beamformers is often limited by the amount of memory resources.

To address this memory limitation, beamforming coefficients can be calculated dynamically and either temporarily stored in a relatively small memory or provided in real-time. A number of such techniques are disclosed, for example, in U.S. Pat. Nos. 5,469,851, 5,653,236, and 8,211,018.

There remains a need for ultrasound system architectures and related methods that can provide a better combination of image quality, frame rate, and scalability. There is a particular need for such system architectures and methods which are suitable for use in handheld or hand-carried devices with embedded electronics.

SUMMARY

In accordance with one or more embodiments, a handheld or hand-carried multibeam ultrasound transducer comprises a plurality of transducer elements in communication with a multiplexer that connects the transducer elements to a plurality of signal conditioning units. The number of signal conditioning units is generally less than, but can also be equal to the number of transducer elements. A plurality of beamformers are connected to the signal conditioning units and are in communication with a single beamformer coefficient generator via a beamformer coefficient bus. Each beamformer provides a plurality of beamforming channels. Each beamforming channel comprises a delay unit operable to delay a signal in the channel and optionally provides a weighting unit to apply a weight. The beamformer coefficient generator provides coefficients to each beamformer in a time-shared manner. The total mass of the machine preferably does not exceed ten pounds (about 4.5 kg).

One aspect of the invention provides ultrasound machines. In some embodiments the ultrasound machines are hand-holdable. The ultrasound machines according to this aspect comprise an ultrasound transmitter and a transducer, connected to the ultrasound transmitter and comprising a plurality of transducer elements. Each of the plurality of transducer elements is operative to generate an output signal in response to receiving ultrasound echo signals. The ultrasound machine includes a plurality of beamformers. Each of the beamformers comprises a plurality of beamformer channels. Each of the plurality of beamformer channels is connected to receive the output signal from a corresponding one of the plurality of transducer elements. The output signal may be digitized upstream from the beamformer channel such that the output signals processed in the beamformer channels each comprise a series of samples. Each of the plurality of beamformer channels comprises a variable delay having an output carrying a delayed value of the corresponding output signal wherein the delayed value is delayed relative to a reference time in an amount determined by a delay value in a first data storage location corresponding to the beamformer channel. The first data storage location is operable to receive and store the delay value for the corresponding beamformer channel. The beamformer comprises a summing circuit connected to receive and sum delayed values of the corresponding output signals to yield a scanline value. The ultrasound machine further comprises a beamformer coefficient generator configured to generate the delay values for the channels of all of the plurality of beamformers. A beamformer coefficient bus is connected between the beamformer coefficient generator and the data storage locations of the plurality of beamformers. A control circuit is configured to control the beamformer coefficient generator to generate and deliver to the corresponding first data locations by way of the beamformer coefficient bus new delay values for the channels of all of the plurality of beamformers during a focal update cycle. A signal processor is connected to receive the scanline values from the plurality of beamformers and to process the scanline values to yield an image.

In some embodiments the ultrasound machine has a mass not exceeding 4½ kilograms. The ultrasound machine may have a housing that supports the transducer and contains the beamformers. The housing may be shaped to facilitate holding the housing by hand. The housing may contain a battery that supplies electrical power to the beamformers.

In some embodiments, each of the beamformer channels comprises a weighting unit including a multiplier connected to multiply the corresponding output signal by a weight determined by a weight value in a second data storage location corresponding to the beamformer channel. The second data storage location is operable to receive and store the weight value for the corresponding beamformer channel. In such embodiments the control circuit may be configured to control the beamformer coefficient generator to generate and deliver to the corresponding second data locations by way of the beamformer coefficient bus new weight values for the channels of all of the plurality of beamformers during the focal update cycle.

In some embodiments the focal update cycle has a duration of 10 microseconds or less.

In some embodiments the beamformer coefficient bus comprises a first plurality of bus lines connected to deliver the new delay values to the first data locations and a second plurality of bus lines connected to deliver the new weight values to the second data locations.

In some embodiments the plurality of beamformers and at least part of the beamformer coefficient bus are provided in a configurable logic device and the ultrasound machine comprises a configuration memory storing configuration information specifying the configurations of the beamformers and beamformer coefficient bus. In such embodiments a number of the plurality of beamformers is user-configurable. For example, the configuration memory may comprise a plurality of sets of configuration information suitable for initializing the configurable logic device to provide various numbers of beamformers. Which set is applied to configure the configurable logic device may be determined based on a user input or determined automatically based on factors such as available battery power.

In some embodiments the ultrasound machine comprises a display connected to display the image. In other embodiments a display is provided on a separate apparatus and the image is connected to the apparatus comprising the display by a wired or wireless data link. For example the ultrasound machine may comprise a wireless transmitter connected to transmit the image for display on a remote display.

In some embodiments a number of the transducer elements exceeds a number of the beamformer channels in each of the beamformers.

In some embodiments the control circuit is operative to trigger the ultrasound transmitter to perform a plurality of transmit events and the signal processor is configured to combine scanline values from different ones of the plurality of transmit events to yield the image. For example, the control circuit may be configured to deliver a first subset of the transducer output signals corresponding to a first aperture to the channels of the beamformers for a first one of the transmit events and to deliver a second subset of the transducer output signals different from the first subset and corresponding to a second aperture to the channels of the beamformers for a second one of the transmit events. As another example, a first one of the transmit events may transmit a first ultrasound pulse having a first amplitude and a second one of the transmit events may transmit a second ultrasound pulse having a second amplitude equal to the first amplitude and a phase that is inverted relative to the first pulse.

In some embodiments a first set comprising two or more of the transmit events each transmit a first ultrasound pulse having a first amplitude and the control circuit is configured to deliver a first subset of the transducer output signals corresponding to a first aperture to the channels of the beamformers for a first one of the first set of transmit events and to deliver a second subset of the transducer output signals different from the first subset and corresponding to a second aperture to the channels of the beamformers for a second one of the first set of transmit events, and a second set comprising two or more other ones of the transmit events each transmit a second ultrasound pulse having the first amplitude and a phase inverted relative to the first pulse, the control circuit is configured to deliver a third subset of the transducer output signals corresponding to a third aperture to the channels of the beamformers for a first one of the second set of transmit events and to deliver a fourth subset of the transducer output signals different from the third subset and corresponding to a fourth aperture to the channels of the beamformers for a second one of the second set of transmit events In some embodiments the plurality of beamformers comprises at least four beamformers.

In some embodiments the variable delay comprises a variable-length first-in, first-out (FIFO) register. In some embodiments the variable delay comprises a coarse delay and an interpolator connected to interpolate between values of successive samples.

In some embodiments the ultrasound machine has a color Doppler mode wherein the transmitter is configured to transmit a series of ultrasound signals in a plurality of transmit events, the plurality of beamformers each yield a scanline comprising a series of the scanline values corresponding to each one of the transmit events, and the signal processor is configured to determine an autocorrelation between corresponding ones of the scanlines generated in response to different ones of the transmit events.

In some embodiments the ultrasound transmitter comprises a transmit beamformer operable to direct transmitted ultrasound toward a transmit focal point located on a line extending from a phase center of the transducer at a first azimuth angle and the beamformer coefficient generator is configured to set the delay values for the channels of the beamformers such that a scanline associated with each of the plurality of beamformers has a different azimuth angle, a different phase center, or both, and the azimuth angles of the scanlines corresponding to the plurality of beamformers are clustered within ±10 degrees of the first azimuth angle. For example, for each image the controller may be configured to control the transmit beamformer to transmit a plurality of ultrasound signals at a corresponding plurality of first azimuth angles and the signal processor is configured to combine the scanline values generated by the plurality of beamformers in response to each of the plurality of transmitted ultrasound signals to yield the image.

Another aspect of the invention provides a method for operating an ultrasound machine. The method comprises: operating an ultrasound transmitter to transmit an ultrasound signal into a volume of interest; receiving echo signals resulting from interaction of the transmitted ultrasound signals with structures in the body of interest at a plurality of transducer elements; passing the received echo signals to each of a plurality of beamformers and, in each of the beamformers at each of a sequence of times: applying selected delays to the echo signals; and summing the delayed echo signals to yield a scanline value; in intervals between the times of the sequence of times, distributing from a beamforming coefficient generator to the beamformers by way of a beamformer coefficient bus new delay values to be applied to the echo signals at a subsequent one of the sequence of times; and processing the scanline values from the plurality of beamformers to yield image data defining an image.

Some embodiments comprise applying weights to the echo signals before summing the echo signals and distributing the weights from the beamforming coefficient generator to the beamformers by way of the beamformer coefficient bus.

In some embodiments completing distributing the delay values and the weights to all of the beamformers is completed in a focal update cycle having a duration of 10 microseconds or less.

The method may comprise displaying the image on a display. This may be done in real time. Displaying the image may comprise wirelessly transmitting the image to a remote display and displaying the image on the remote display.

In some embodiments the method comprises configuring a configurable logic device to provide the beamformers and the beamformer coefficient bus. In some embodiments the method comprises configuring a configurable logic device to provide the beamformer coefficient generator. The configurable logic device may, for example, comprise a field programmable gate array (FPGA). In some embodiments the method comprises configuring the configurable logic device to provide a user-selected number of the beamformers.

In some embodiments the method comprises operating the ultrasound transmitter to transmit a sequence comprising a plurality of ultrasound signals into the volume of interest; and combining scanline values derived from echo signals of different ones of the plurality of transmitted ultrasound signals to yield the image. For example, a method according to an example embodiment comprises: for a first one of the transmit signals delivering a first subset of the transducer output signals corresponding to a first aperture to the channels of the beamformers; and for a second one of the transmit signals delivering a second subset of the transducer output signals different from the first subset and corresponding to a second aperture to the channels of the beamformers. In another example a first one of the transmit signals comprises a first ultrasound pulse having a first amplitude and a second one of the transmit signals comprises a second ultrasound pulse having a second amplitude equal to the first amplitude and a phase that is inverted relative to the first pulse. In another example a first set comprising two or more of the transmit signals each comprise a first ultrasound pulse having a first amplitude and the method delivers a first subset of the transducer output signals corresponding to a first aperture to the channels of the beamformers for a first one of the first set of transmit events and delivers a second subset of the transducer output signals different from the first subset and corresponding to a second aperture to the channels of the beamformers for a second one of the first set of transmit events, and a second set comprising two or more other ones of the transmit events each transmit a second ultrasound pulse having the first amplitude and a phase inverted relative to the first pulse and the method delivers a third subset of the transducer output signals corresponding to a third aperture to the channels of the beamformers for a first one of the second set of transmit events and delivers a fourth subset of the transducer output signals different from the third subset and corresponding to a fourth aperture to the channels of the beamformers for a second one of the second set of transmit events.

In some embodiments applying the selected delays to the echo signals comprises passing the echo signals through variable-length first-in, first-out (FIFO) registers. In some embodiments applying the selected delays further comprises interpolating between values of successive samples.

In some embodiments the method comprises performing color Doppler imaging by transmitting a series of ultrasound signals in a plurality of transmit events, for each one of the transmit events obtaining from the beamformers a plurality of scanlines each comprising a series of the scanline values, and determining an autocorrelation between corresponding ones of the scanlines generated in response to different ones of the transmit events.

In some embodiments operating the ultrasound transmitter to transmit an ultrasound signal comprises focusing the ultrasound signal toward a transmit focal point located on a line extending from a phase center of a transducer containing the transducer elements at a first azimuth angle and the method comprises setting the selected delays such that a scanline associated with each of the plurality of beamformers has a different azimuth angle, a different phase center, or both, and the azimuth angles of the scanlines corresponding to the plurality of beamformers are clustered within ±10 degrees of the first azimuth angle. For example, for each image the method may comprise transmitting a plurality of the transmit ultrasound signals at a corresponding plurality of first azimuth angles and combining the scanline values generated by the plurality of beamformers in response to each of the plurality of transmitted ultrasound signals to yield the image.

Another aspect of the invention provides a handheld ultrasound imaging machine comprising: a transducer array comprising a plurality of transducer elements; a signal conditioning unit connected to receive signals from the transducer array; a plurality of beamformers connected to receive conditioned signals output by the signal conditioning unit; a signal processor connected to receive beamformed scanline values output by the beamformers; a display device connected to the signal processor; and a common source of channel-dependent parameters connected to supply different channel-dependent parameters to each of the beamformers; and a scan controller. Each of the beamformers comprises multiple beamformer channels each comprising a signal delay device, a memory device for storing a channel-dependent parameter; and a beamforming delay processor for controlling the amount of delay produced by the signal delay device based on the channel-dependent parameter. The beamforming delay processors operate in parallel, and the source of beam-dependent parameters comprises a beamformer coefficient generator which operates in a time-shared fashion and distributes the channel-dependent parameters to the memory devices of the beamformers by way of a beamforming coefficient bus. In some embodiments the entire system has a mass of less than 4.5 kg.

In some embodiments the beamformer coefficient bus comprises lines carrying a delay and lines carrying a weight connected to each of the memory devices and lines carrying an enable signal for each channel of each beamformer. In some embodiments the beamformer coefficient generator includes a means for calculating the difference in time-of-flight for ultrasound signals.

Another aspect of the invention provides a method for generating and distributing one or more beamforming parameters to a plurality of beamformers in a handheld ultrasound machine. The method comprises calculating beamforming parameters for a plurality of beamformers; and distributing different sets of the beamforming parameters to each of a plurality of beamformers via a beamformer coefficient bus. In some embodiments the method comprises: at each of the beamformers storing the beamforming parameters of the corresponding set of beamforming parameters within a storage device within the beamformer based on a beamformer enable signal carried on the beamformer coefficient bus. The beamforming parameters may include delays for beamformer channels and/or weights for the beamformer channels.

Further aspects and example embodiments are illustrated in the accompanying drawings and/or described in the following description.

Advantages

Thus several advantages of one or more aspects are to provide an ultrasound architecture that:
a) enables multibeam formation within a portable probe;
b) is scalable to a greater number of beamformers; and
c) has improved image resolution and frame rate compared to traditional handheld machines with single-beamformer architectures.

These and other advantages of one or more aspects will become apparent from a consideration of the ensuing description and accompanying drawings.

The description of the invention which follows, together with the accompanying drawings should not be construed as limiting the invention to the examples shown and described, because those skilled in the art to which this invention pertains will be able to devise other forms thereof within the scope of the appended claims.

BRIEF DESCRIPTION OF THE DRAWINGS

The accompanying drawings illustrate non-limiting example embodiments of the invention.

LIST OF REFERENCES

100 - Portable ultrasound machine
102 - Transducer array
104 - Transducer element
106 - Transmit/Receive (T/R) switch
108 - Transmitter
110 - Signal conditioning unit
112 - Coefficient Memory
114 - Receive beamformer
116 - Signal processor
118 - Data link
120 - Display device
122 - Scan controller
200 - Portable ultrasound machine
202 - Beamformer coefficient generator
204 - Beamformer coefficient bus
206 - RF data bus
300 - Coefficient generator controller
302 - Channel index counter
304 - Beamformer index counter
306 - Element position memory
308 - Focal point tracker
310 - Delay calculator
312 - Delay
314 - Apodization calculator
316 - Apodization memory
318 - Weight
320 - Beamformer enable address
322 - Focal update sync
400 - Storage register
402 - Focal update register
404 - Delay Controller
406 - Coarse delay unit
408 - Fine delay unit
410 - Weighting unit
412 - Summer
414 - Beamformed data
700 - Configuration memory

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

This invention provides a beamforming architecture for an ultrasonic imaging machine. The architecture is optimised to enable various methods to improve penetration, signal-to-noise ratio, resolution, and frame rate.

Figure 1:
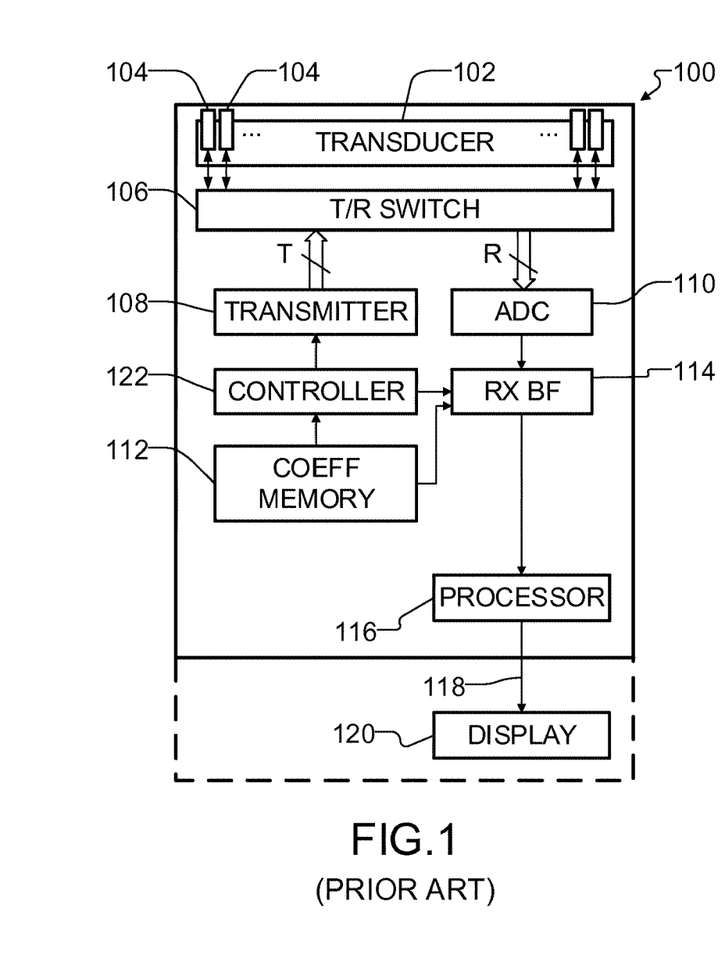
FIG. 1 is a functional block diagram of a typical prior art handheld or hand-carried medical ultrasound machine.

A typical handheld or hand-carried ultrasound machine 100 is illustrated in block diagram form in FIG. 1. Machine 100 includes a transducer array 102 that comprises a plurality of transducer elements 104. Transducer elements 104 are operable to both emit and receive ultrasound energy. When energized by a transmitter 108, the transducer elements 104 produce a burst of ultrasonic energy. To conserve space, power, and cost, often only a subset of transducer elements 104 are active for a particular transmit event. This subset of elements forms a transmit aperture.

The ultrasound energy produced by transducer array 102 is directed toward a body region of a patient containing a volume of interest. Some of the ultrasound energy is then reflected back to transducer array 102 as echo signals. Again, to conserve space, power, and cost, often a subset of transducer elements are used to receive the echo signals; this subset of elements form the receive aperture. The transducer elements 104 in the receive aperture convert the received ultrasound energy into analog electrical signals which are then sent through a set of transmit/receive (T/R) switches 106 to yield N channels of echo data. A set of analog-to-digital converters (ADCs) 110 digitises the analog signals from the switches. The digitised signals are then sent to a receive beamformer 114.

Transmitter 108 and receive beamformer 114 are operated under the control of a scan controller 122. Receive beamformer 114 combines the separate echo signals from each channel using pre-calculated delay and weight values stored in coefficient memory 112 to yield a single echo signal which represents the received energy from a particular scanline.

Under the direction of the scan controller 122, the machine generates and processes additional transmit and receive events to produce the multiple scanlines required to form an image. Ultrasound images are typically made up of 50 to a few hundred lines. Lateral resolution can be improved by increasing the number of lines in each image. However, increasing the number of lines tends to reduce the achievable frame rate. It is not mandatory that the scanlines and/or transmit beams originate at the center of the transducer. For example, where the transducer comprises a linear array or curved array of transducer elements, receive apertures and delays may be selected such that scanlines are parallel to one another. For example, all or a number of the scanlines may be parallel to the transmit beam.

A signal processor 116 is in communication with the receive beamformer 114 and applies the necessary processing steps to combine multiple scanlines from these different transmit events to yield image data. Signal processor 116 communicates this image data via a data link 118 to a display device 120. Data link 118 may comprise a cable, a wireless connection, or the like. Display device 120 displays the ultrasound image to the user. An example of such an architecture is described in U.S. Pat. No. 5,722,412, issued Mar. 3, 1998 to Pflugrafth et al.

Figure 2:
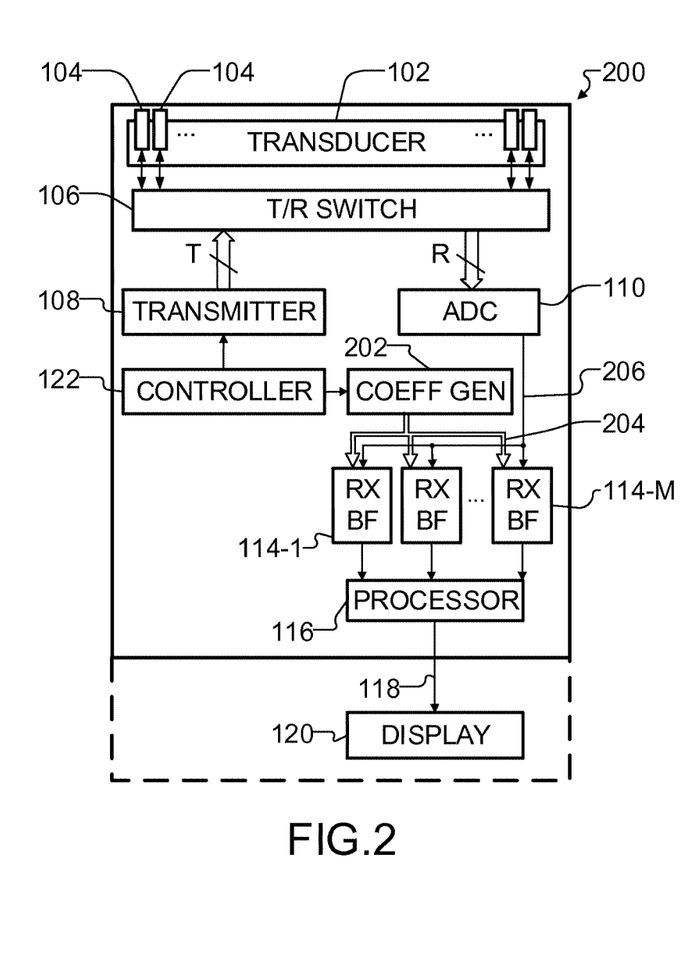
FIG. 2 is a functional block diagram of a handheld or hand-carried medical ultrasound machine including a time-shared beamformer coefficient generator that supplies a plurality of beamformers according to certain embodiments of the present disclosure.

FIG. 2 illustrates an ultrasonic imaging machine 200 with a beamforming architecture in accordance with some embodiments of the present invention. Imaging machine 200 may be handheld or hand-carried. Imaging machine 200 comprises a time-shared beamforming coefficient generator 202, shown in more detail in FIG. 3, which dynamically calculates delay or delay and weight values for each channel. The delay and weight values for each channel are based on the origin and direction of the beam, the speed of propagation of the beam in the tissue, and the location of the receive element corresponding to the channel relative to the beam. Examples of these calculations are described in more detail below.

The delay and weight values are communicated via a beamforming coefficient bus 204 to a plurality of beamformers 144-1 to 144-M (collectively beamformers 144). The structure and operation of the beamformers are shown in more detail in FIG. 4 and described below. The beamformed data produced by each beamformer may be further processed in a manner similar to that in the typical ultrasound machine described above. The beamformed data for different scanlines are combined by signal processor 116 to yield ultrasound image data which is then communicated via data link 118 to display device 120 where the image data is formed into an image on display device 120.

Figure 3:
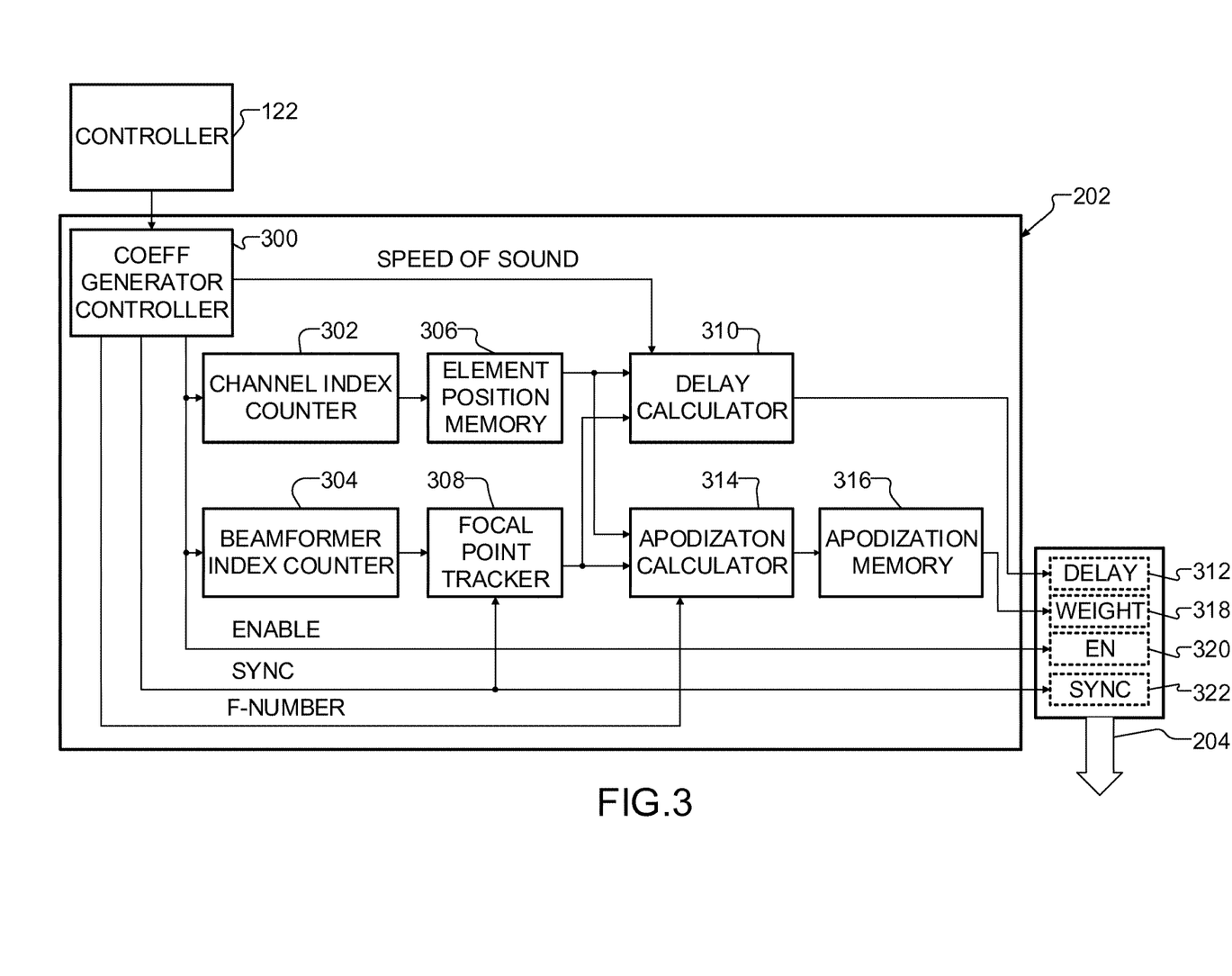
FIG. 3 is a functional block diagram of a beamformer coefficient generator according to certain embodiments of the present disclosure.

FIG. 3 illustrates an example beamformer coefficient generator 202. Beamformer coefficient generator 202 dynamically calculates a delay and weight value for each channel of each beamformer based on information about the scan, then distributes these delay and weight values to each beamformer 114 via a beamforming coefficient bus 204. Beamformer coefficient generator 202 comprises a coefficient generator controller 300, which uses information from scan controller 122 to provide beam- and channel-dependent parameters to a focal point tracker 308, a delay calculator 310, and an apodization calculator 314. The beam-dependent parameters may include, but are not limited to: phase center, beam angle, and F-number. The channel-specific parameters may include, but are not limited to, the physical position of the transducer element 104 that corresponds to the channel.

Focal point tracker 308 determines the location of the focal point based on the beam-dependent parameters and the time elapsed since the transmit event. Delay calculator 310 calculates a delay 312 to apply to an echo signal on a channel so that it can be coherently summed with echo signals from other channels. This calculation is based on the focal point, the location of the transducer element the echo was received on, and the phase center. An example delay calculation is described below. Apodization calculator 314 calculates a weight 318 to attenuate or amplify the echo signal for a particular channel. Weight 318 can be used, for example, to attenuate echo signals received at transducer elements located far from the beam to reduce side lobes. The weight calculation is based on the element position, focal point position, and F-number. F-number is the ratio of the imaging depth to the aperture size. An example weight calculation is described below. Once calculated, the delay 312 and weight 318 are distributed via the beamforming coefficient bus 204.

In some embodiments, beamforming coefficient bus 204 may be a multi-bit bus comprising several buses and may be implemented in a programmable logic device. For example, beamforming coefficient bus 204 may comprise a 14 bit bus for delay 312, a 14 bit bus for weight 318, a 1 bit bus for each channel of each beamformer (i.e., M×N buses) collectively forming beamformer enable address 320 and a 1 bit bus for focal update sync 322.

In some embodiments, coefficient generator controller 300 receives parameters from the scan controller 122. These parameters may comprise, for example: beam directions, channel mux info, F-number, and timing information. The beam direction for a beam indicates the phase center, and angle of the beam relative to the transducer array. The channel mux info maps which transducer element 104 corresponds to which data channel.

Figure 5:
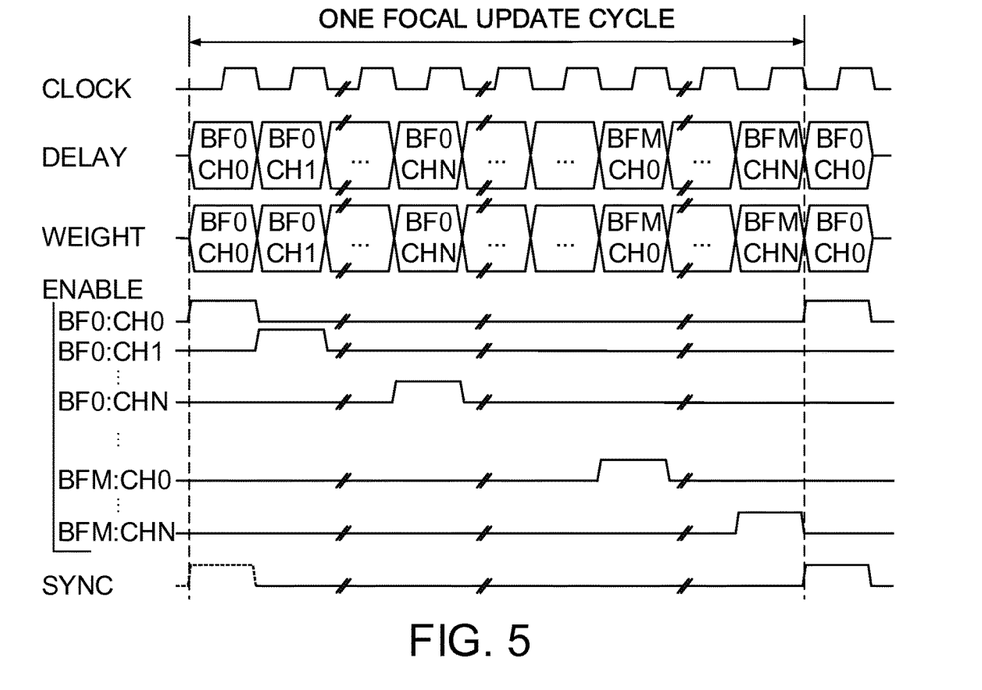
FIG. 5 is a timing diagram that illustrates the operation of the beamformer coefficient generator according to certain embodiments of the present disclosure.

In an example embodiment, delay 312 and weight 318 for each channel of each beamformer are all updated within a focal update cycle. To achieve this, coefficient generator controller 300 generates a beamformer enable address 320 which cycles through each of the data channels within each beamformer. The delay 312 and weight 318 for the current beamformer/channel are presented on beamforming coefficient bus 204 together with the corresponding ENABLE signal on beamformer enable address 320. One example timing is illustrated in FIG. 5.

For each beamformer/channel iteration, the beamformer enable address 320 is communicated to a channel index counter 302 and beamformer index counter 304 (see FIG. 3), which convert the beamformer enable into the appropriate channel index, and beamformer index, respectively. Channel index counter 302 is connected to an element position memory 306 which contains the appropriate element position. Beamformer index counter 304 is connected to focal point tracker 308 which also receives a focal update sync 322 from coefficient generator controller 300. Element position memory 306 and the focal point tracker 308 provide the element position and focal point position to a distance calculator 310. Distance calculator 310 calculates a delay 314 to correct for the difference in time-of-flight between the phase center and the current element. The element position and focal point position are also supplied to an apodization calculator 314, which generates an address within an apodization memory 316 that contains an appropriate weight 318. The delay 312 and weight 318 are applied along with the beamformer enable address 320 and the focal update sync 322 to the beamformer coefficient bus 204.

Dynamic Delay and Weight Calculation

Figure 6:
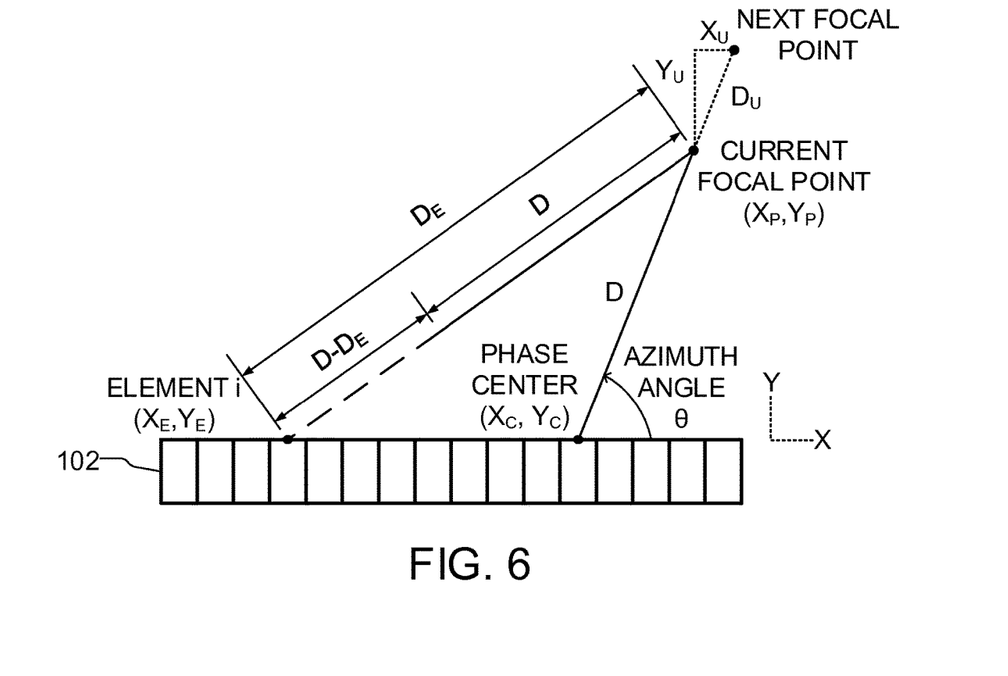
FIG. 6 is an illustration of the geometry used to calculate the difference in time-of-flight.

Equations that may be applied for calculating the time-of-flight delay and aperture weighting are well known by those skilled in the art. The geometry used herein is shown in FIG. 6 for a linear transducer. For a particular beam represented by a phase center $P_C$ and an angle $\theta$, the time t required for ultrasound energy to travel to a focal point along the beam $(X_P, Y_P)$ and return as an echo is a function of the distance D and speed of sound in the imaged media, c:

$$t = \frac{2D}{c} \qquad 1$$

To track the focal point over time, the incremental distance $D_U$ traveled by the focal point during each focal update cycle is calculated based on the focal update frequency $f_U$:

$$D_U = \frac{c}{2f_U} \qquad 2$$

The horizontal $X_U$ and vertical $Y_U$ components of the incremental distance can then be calculated using the beam angle:

$$X_U = D_U \cos\theta \qquad 3$$

$$Y_U = D_U \sin\theta \qquad 4$$

Focal point tracker 308 calculates the position of the next focal point based on the previous focal point and the incremental definition of the beam. Focal point tracker 308 is initialized with the starting point of the beam and zero distance:

$$X(0) = X_C \qquad 5$$

$$Y(0) = Y_C \qquad 6$$

$$D(0) = 0 \qquad 7$$

The current focal point can then be calculated for each subsequent focal update cycle:

$$X(t) = X(t-1) + X_U \qquad 8$$

$$Y(t) = Y(t-1) + Y_U \qquad 9$$

$$D(t) = D(t-1) + D_U \qquad 10$$

Delay Calculation

Delay calculator 310 calculates the difference in time-of-flight between the phase center for a beam and a given element by calculating the difference in distance traveled. First, the distance from the transducer element of channel j to the focal point is calculated using the current focal position (X(t), Y(t)) and the position of the element stored in memory $(X_E(j), Y_E(j))$:

$$D_e(t,j) = \sqrt{(X(t)-X_E(j))^2 + (Y(t)-Y_E(j))^2} \qquad 11$$

The delay distance $D_D$ is found as the difference between the distance between the element and the focal point (from Equation 11) and the distance from the focal point to the phase center (From Equation 10):

$$D_D(t,j) = D(t) - D_E(t,j) \qquad 12$$

This distance is then converted to an integer number of fractional period delay cycles that represent the fine delay:

$$n_f = \text{floor}(K_1 + K_2 \times D_D) \qquad 13$$

where $K_1$ is the baseline constant delay value for a virtual element situated at the phase center (i.e., $X_C, Y_C$) and $K_2$ is a function of the speed of sound in tissue.

Weight Calculation

Apodization calculator 314 calculates the weight applied to each echo signal. The aperture position A is calculated based on the current focal point distance, the F-number, and the initial distance of the transducer element from the phase center:

$$A(t) = \left(D(t) \times \frac{1}{f}\right) - \sqrt{(X_C - X_E(j))^2 + (Y_C - Y_E(j))^2} \qquad 14$$

While the focal point is less than the initial distance, i.e. aperture position is less than zero, the aperture is closed and a weight of zero is applied. As the focal point moves further away, the aperture position is used to select the appropriate weight and is eventually bounded. In one embodiment, the aperture position is used to address an apodization table stored in memory. For example, the relation between aperture position and aperture address for an apodization memory 316 with 512 elements may be as follows:

$$ApertureID = \begin{cases} 0 & A < 0 \\ \frac{A}{64} & 0 \le \frac{A}{64} \le 511 \\ 511 & \frac{A}{64} > 511 \end{cases} \qquad 15$$

The ApertureID is an address of a windowing function stored in memory that contains the appropriate weights. One skilled in the art can imagine various modifications, such as using different windowing functions, differently sized tables, or dynamically calculated values.

Figure 4:
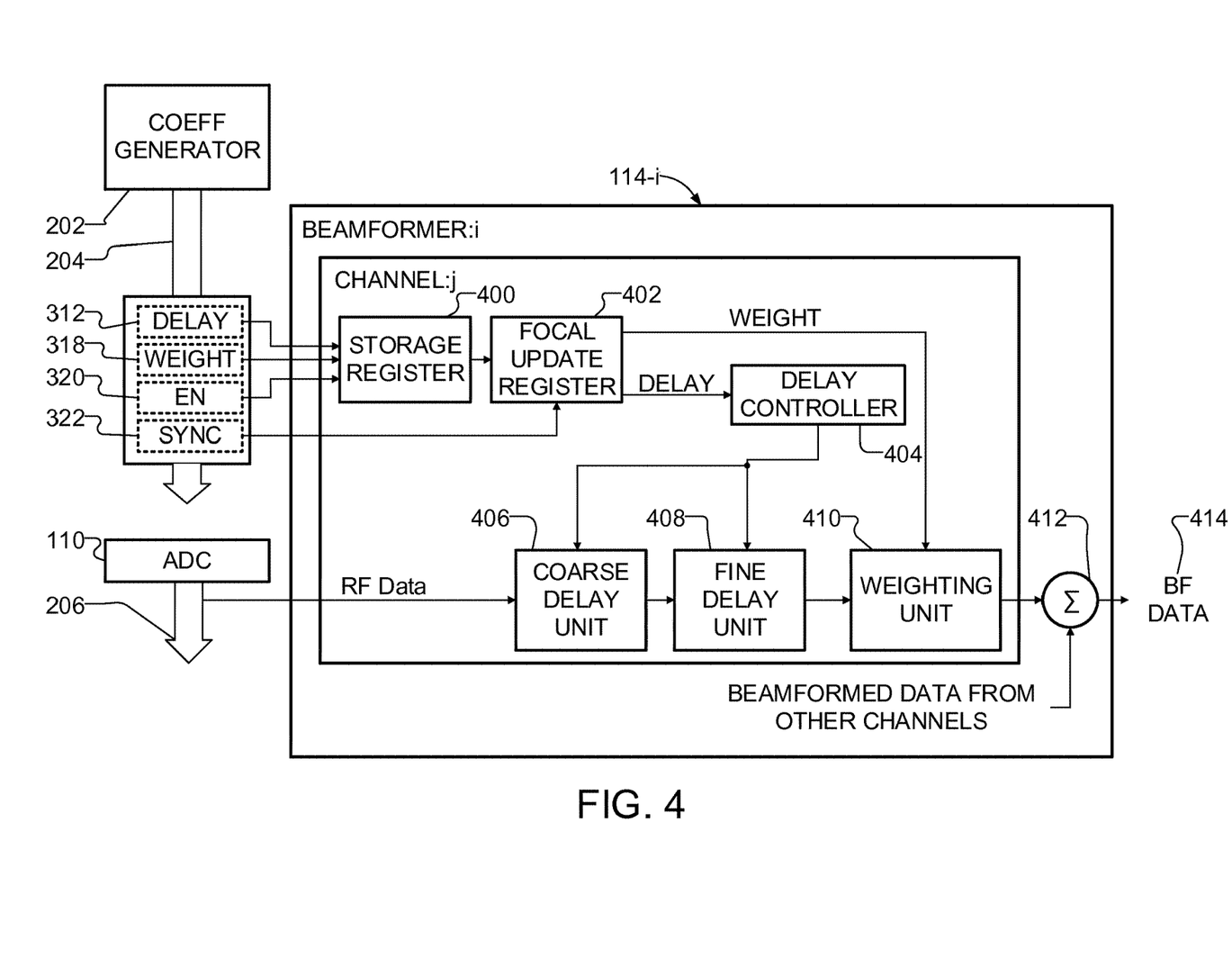
FIG. 4 is a functional block diagram of a digital beamformer according to certain embodiments of the present disclosure.

A single receive beamformer 114 in accordance with one or more embodiments of the present invention is illustrated in FIG. 4. Receive beamformer 114 performs delay and sum beamforming on the echo signals so they can be summed coherently. Each beamformer 114 is connected to the beamformer coefficient generator 202 via beamformer coefficient bus 204 and to signal conditioning unit 110 via ADC bus 206. ADC bus 206 communicates RF data from the appropriate channel to the delay and sum circuitry. The delay 312 and weight 318 from the beamformer coefficient bus 204 for the next focal point are stored within a storage register 400. When the focal update sync 322 is asserted, the delay and weight in storage register 400 are moved to a focal update register 402. Focal update register 402 communicates the delay to a delay controller 404, which controls a coarse delay unit 406 and fine delay unit 408. Coarse delay unit 406 and fine delay unit 408 apply the appropriate delay to the RF signal. Focal update register 402 also supplies the weight to a weighting unit 410 which applies the appropriate weight to the delayed RF signal. The delayed and weighted RF signal is then sent to a summer 412 where it is combined with the delayed and weighed RF signals from the other channels of the beamformer to form beamformed data 414.

Coarse delay unit 406 may be implemented using a FIFO register. The FIFO register contains a data input line, a data output line, a read enable, a write enable, a clock, and a size indicator. The delay controller 404 introduces a variable delay to the data for a particular element by controlling the size of the FIFO register based on the coarse delay value. The coarse delay value is represented as an integer number of clock cycles. During each clock cycle, the coarse delay value is compared to the size of the FIFO register. If the delay is larger than the current size of the FIFO, the write enable is stalled, increasing the size of the FIFO. The maximum length of the FIFO can be adjusted based on the available memory resources, but usually a maximum size of 2068 or fewer samples will suffice. As the focal point moves further away from the transducer, the relative delay between channels decreases. Once the delay is smaller than the FIFO register size, the write is enabled, which applies the appropriate amount of delay to the signal.

Fine delay unit 408 may comprise an interpolator that combines successive samples to achieve sub-system clock delays, such as disclosed by U.S. Pat. No. 4,787,392 issued Nov. 29, 1988 to Saugeon. In a presently preferred embodiment, fine delay unit 408 comprises a four-stage interpolator and is used to achieve a fine delay of one quarter of the sampling period.

FIG. 5 illustrates one embodiment for the time sharing of beamformer coefficient bus 204 where the beamformer coefficient generator 202 calculates the delays and weights in a sequential manner. During each clock cycle, the delay and weight for a given beamformer and channel are calculated. A corresponding ENABLE signal ensures the beamforming coefficients are written to the correct register. In this embodiment, the coefficients are calculated by sequencing through all channels within a particular beamformer before sequencing through the channels of the next beamformer. When all the coefficients have been calculated, a SYNC signal ensures that all beamformers 114 use the updated values. The focal update rate is thus a function of the product of the number of channels and the number of beamformers.

For example, with a 240 MHz clock, 8 beamformers, and 32 channels, it may take 256 clock cycles or approximately 1.1 microseconds to calculate all the necessary beamforming parameters and to load those parameters into the 8 beamformers. This is equivalent to a focal update depth, or focal update resolution, of 1.6 mm. Those skilled in the art will see that the focal update depth can be optimised by modifying the sampling rate. Accordingly, the focal update duration in some embodiments is less than about 10 microseconds. In some embodiments a focal update is completed in less than about 1 microsecond.

Figure 7:
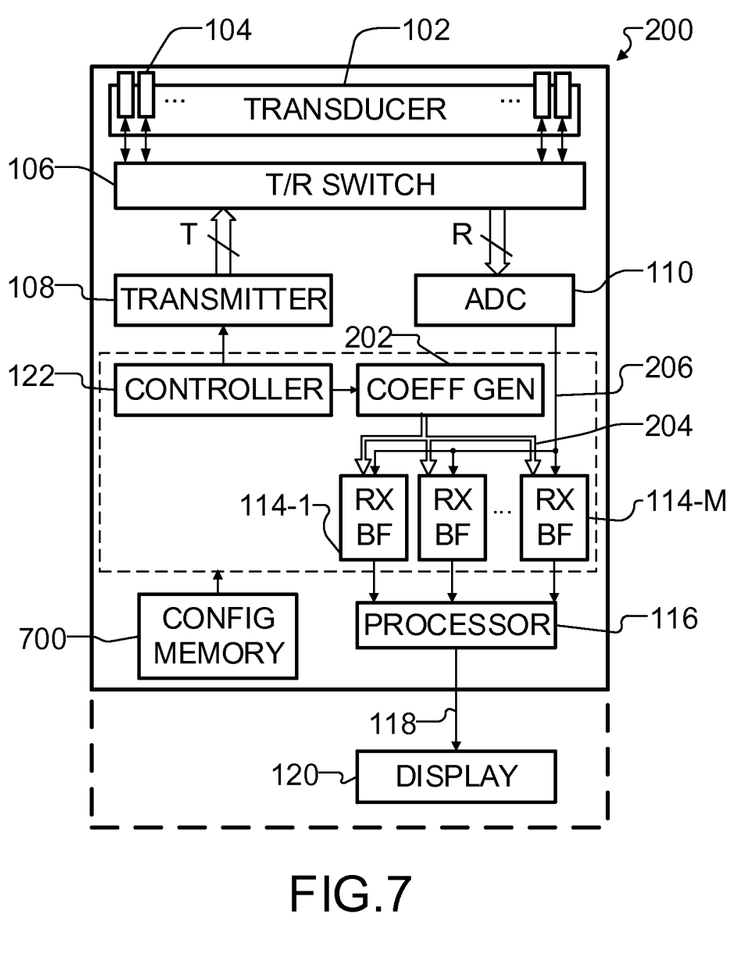
FIG. 7 is a functional block diagram of a handheld or hand-carried medical ultrasound machine according to certain embodiments of the present disclosure.

FIG. 7 illustrates one embodiments of the ultrasound machine 200 where beamformers 114 are implemented in a programmable logic device, such as a field programmable gate array (FPGA). Configuration information such as, but not limited to, the number of beamformers and the number of channels, may be stored in a configuration memory 700 in communication with scan controller 122. The number of beamformers 114, M, may be predetermined and constant, or variable. For example, the number of beamformers could be changed by the user and/or changed automatically in response to a signal such as power level.

Alternatively, beamformer 114 could be implemented on an application specific integrated circuit (ASIC). Since the beamformer does not include the complexity of the delay and weight calculators, a suitable beamformer may comprise only simple logic and a small amount of memory, requiring limited logic resources. Since fewer logic resources are required for each beamformer, the system is scalable to a larger number of beamformers than might otherwise be practical.

In embodiments where beamformers are provided by configuring an FPGA or other configurable logic device, it is only necessary to configure the logic device to provide a desired number of beamformers. For example, different configurations of the logic device may provide 2, 4, 8 or 16 beamformers (note the number of beamformers is not limited to powers of two, these are just convenient examples). The configurable logic device may also be configured to provide connections of the beamformer coefficient bus to each of the beamformers.

In embodiments where beamformers are provided in ASICs or other hard-wired configurations, the number of beamformers that are active may be varied. Non-active beamformers may be shut off or run in a standby mode to save power. In such embodiments, when the number of active beamformers is changed the operation of the beamformer coefficient generator may also be changed such that beamformer coefficients are generated and/or distributed only for the ones of the beamformers that are currently active.

One advantage of one or more embodiments is the ability of the handheld or hand-carried ultrasonic imaging machine to enable pulse inversion harmonic imaging with a small receive aperture at full frame rate. For example, a typical full-sized diagnostic ultrasound machine with a high channel count (e.g., 192) using 1 transmit/receive event per line and imaging at a penetration depth of 15 cm may be able to produce a 192 line B-mode ultrasound image at a frame rate in the range of 25 Hz. Using pulse inversion harmonic imaging to improve the signal-to-noise ratio requires 2 transmit/receive events per line, which would reduce the frame rate to approximately 13 Hz. In a handheld or hand-carried machine with a limited number of receive channels (e.g., 32), multiple transmit/receive events (e.g., 2) are typically required to form a synthetic aperture large enough (e.g., 64 elements) to provide adequate sensitivity to produce each line. Hence, producing an image on the portable machine comparable in quality to images obtained by the full-sized diagnostic ultrasound machine would be limited to a frame rate of approximately 6 Hz, which is unusably low for most applications.

In an embodiment of the handheld or hand-carried machine architecture, with, for example, 8 beamformers, the machine uses 4 transmit/receive events to generate each line (i.e., 2 for the pulse inversion and 2 for synthetic aperture), creating a 192 line image at a frame rate of 50 Hz. Additional image quality can be achieved by overlapping subsequent apertures, by for example, 4 lines at a time, yielding a frame rate of 25 Hz. This frame rate is comparable to the high channel count ultrasound imaging machine using 1 transmit/receive event per line.

Another advantage of one or more embodiments is the ability of the handheld or hand-carried ultrasonic imaging machine to provide high-quality color Doppler images from a small receive aperture at relatively fast frame rates. Doppler signals from blood motion are usually weak and difficult to detect using a small aperture. Color Doppler imaging is a well-known technique that employs sequences that transmit and receive the same ultrasound line several times and performs autocorrelation to estimate the speed of flow of fluids such as blood. To maintain frame rates above 8-10 Hz, the number of times a single color line can be transmitted/received is usually limited to 8-10 times. An embodiment of the present handheld or hand-carried ultrasonic imaging machine may be configured with 8 beamformers, and despite receiving through a small receive aperture (e.g. 32 elements), is able to do 4 to 8 times more line repetitions to estimate flow speed for a similar frame rate. With a dataset of 64 line repetitions, despite a smaller receive aperture, the autocorrelation algorithm to produce a speed value can be as robust as a high channel count ultrasound imaging machine.

Since handheld or hand-carried ultrasonic imaging machines typically rely on battery power, managing power consumption is very important for performance. Yet another advantage of one or more embodiments is the ability of the handheld or hand-carried ultrasonic imaging machine to provide high-quality images at a fraction of the power consumption of typical machines. Transmitting the ultrasound waves requires a substantial amount of power, and using multiple receive beams enables more data to be produced for each transmit event. Since the beamformers of the present invention also share the same beamforming coefficient generator, the total power consumption used for beamforming is less than the power consumption of a traditional multibeam implementation which relies on duplicated hardware or large amounts of memory. In such an embodiment, frame rate is specified, for example 25 Hz, and the machine adjusts the time between transmit/receive events to match that frame rate for a given number of lines. For example, with 8 lines acquired, overlapping by 4 lines at a time, only ¼ of the transmit events are required for a similar resolution, resulting in less power consumption and no decrease in image quality.

Accordingly the reader will see that according to one embodiment of the invention, we have provided an apparatus comprising a beamforming coefficient generator that dynamically calculates the delay and weight coefficients necessary to process multiple receive beams in parallel. This enables the ultrasound diagnostic device to produce images at a high frame rate and of high image quality while satisfying the small space and low power consumption restrictions of a handheld or hand-carried device.

While the above description contains many specifications, these should not be construed as limitations on the scope of any embodiment, but as exemplifications of various embodiments thereof. Many other ramifications and variations are possible within the teachings of the various embodiments.

Thus the scope should be determined by the appended claims and their legal equivalents, and not by the examples given.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), field programmable gate arrays ("FPGAs"), and complex programmable logic devices ("CPLDs"). Examples of programmable data processors are: microcontrollers, microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Certain aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, solid-state drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, some aspects of the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for operating an ultrasound machine, the method comprising:
    operating an ultrasound transmitter to transmit an ultrasound signal into a volume of interest;
    receiving echo signals resulting from interaction of the transmitted ultrasound signal with structures in the volume of interest at a plurality of transducer elements;
    passing the received echo signals to each of a plurality of beamformers and, in each of the beamformers at each of a sequence of times:
        applying delays to the echo signals; and
        summing the delayed echo signals to yield a scanline value;
    in intervals between the times of the sequence of times, distributing from a beamforming coefficient generator common amongst the plurality of the beamformers, by way of a beamformer coefficient bus, new delay values to be applied to the echo signals at a subsequent one of the sequence of times, wherein the common beamforming coefficient generator calculates the delays to be applied to every echo signal passed to each of the plurality of beamformers; and
    processing the scanline values from the plurality of beamformers to yield image data defining an image.

2. A method according to claim 1 comprising applying weights to the echo signals before summing the echo signals and distributing the weights from the beamforming coefficient generator to the beamformers by way of the beamformer coefficient bus.

3. A method according to claim 2 wherein completing distributing the delay values and the weights to all of the beamformers is completed in a focal update cycle having a duration of 10 microseconds or less.

4. A method according to claim 1 comprising displaying the image on a display.

5. A method according to claim 1 comprising wirelessly transmitting the image to a remote display and displaying the image on the remote display.

6. A method according to claim 1 wherein there are at least four of the beamformers.

7. A method according to claim 1 wherein the beamformers and the beamformer coefficient bus are provided by way of a programmed configurable logic device.

8. A method according to claim 7 wherein the beamformer coefficient generator is provided by way of a programmed configurable logic device.

9. A method according to claim 7 wherein a number of the plurality of beamformers is user-selectable.

10. A method according to claim 1 comprising performing color Doppler imaging by transmitting a series of ultrasound signals in a plurality of transmit events, for each one of the transmit events obtaining from the beamformers a plurality of scanlines each comprising a series of the scanline values, and determining an autocorrelation between corresponding ones of the scanlines generated in response to different ones of the transmit events.

11. A method according to claim 1 wherein operating the ultrasound transmitter to transmit an ultrasound signal comprises focusing the ultrasound signal toward a transmit focal point located on a line extending from a phase center of a transducer containing the transducer elements at a first azimuth angle and the method comprises setting the selected delays such that a scanline associated with each of the plurality of beamformers has a different azimuth angle, a different phase center, or both, and the azimuth angles of the scanlines corresponding to the plurality of beamformers are clustered within ±10 degrees of the first azimuth angle.

12. A method according to claim 11, wherein the method further comprises transmitting a plurality of the transmit ultrasound signals at a corresponding plurality of first azimuth angles and combining the scanline values generated by the plurality of beamformers in response to each of the plurality of transmitted ultrasound signals to yield the image.

13. A method according to claim 1, wherein the method is performed by a portable ultrasound machine having a mass not exceeding 4½ kilograms.

14. A method according to claim 1, wherein a number of the plurality of transducer elements exceeds a number of beamformer channels in each of the beamformers.

15. A method according to claim 1 comprising operating the ultrasound transmitter to transmit a sequence comprising a plurality of ultrasound signals into the volume of interest; and combining scanline values derived from echo signals of different ones of the plurality of transmitted ultrasound signals to yield the image.

16. A method according to claim 15 wherein a first one of the transmit signals comprises a first ultrasound pulse having a first amplitude and a second one of the transmit signals comprises a second ultrasound pulse having a second amplitude equal to the first amplitude and a phase that is inverted relative to the first pulse.

17. A method according to claim 15 wherein the plurality of beamformers each comprise a plurality of channels, and wherein:
 a first set comprising two or more of the transmit signals each comprise a first ultrasound pulse having a first amplitude and the method delivers a first subset of the received echo signals corresponding to a first aperture to the channels of the beamformers for a first one of the first set of transmit signals and delivers a second subset of the received echo signals different from the first subset and corresponding to a second aperture to the channels of the beamformers for a second one of the first set of transmit signals, and
 a second set comprising two or more other ones of the transmit signals each transmit a second ultrasound pulse having the first amplitude and a phase inverted relative to the first pulse and the method delivers a third subset of the received echo signals corresponding to a third aperture to the channels of the beamformers for a first one of the second set of transmit signals and delivers a fourth subset of the received echo signals different from the third subset and corresponding to a fourth aperture to the channels of the beamformers for a second one of the second set of transmit signals.

18. A method according to claim 15, wherein the plurality of beamformers each comprise a plurality of channels, and wherein the method further comprises:
 for a first one of the transmit signals delivering a first subset of the received echo signals corresponding to a first aperture to the channels of the beamformers; and
 for a second one of the transmit signals delivering a second subset of the received echo signals different from the first subset and corresponding to a second aperture to the channels of the beamformers.

19. A method according to claim 1 wherein applying the selected delays to the echo signals comprises passing the echo signals through variable-length first-in, first-out (FIFO) registers.

20. A method according to claim 19 wherein applying the selected delays further comprises interpolating values of successive samples.

21. An ultrasound machine comprising:
 an ultrasound transmitter;
 a plurality of transducer elements connected to the ultrasound transmitter; and
 a plurality of beamformers, wherein each of the beamformers are configured to receive signals from one or more of the plurality of transducer elements;
 wherein, during operation of the ultrasound machine, the ultrasound machine is configured to:
  operate the ultrasound transmitter to transmit an ultrasound signal into a volume of interest;
  receive, at the one or more transducer elements, echo signals resulting from interaction of the transmitted ultrasound signal with structures in the volume of interest at the plurality of transducer elements;
  pass, from the one or more transducer elements, the received echo signals to each of the plurality of beamformers and, in each of the beamformers at each of a sequence of times:
   apply delays to the echo signals; and
   sum the delayed echo signals to yield a scanline value;
  in intervals between the times of the sequence of times, distribute from a beamforming coefficient generator common amongst the plurality of the beamformers, by way of a beamformer coefficient bus, new delay values to be applied to the echo signals at a subsequent one of the sequence of times, wherein the common beamforming coefficient generator calculates the delays to be applied to every echo signal passed to each of the plurality of beamformers; and
  process the scanline values from the plurality of beamformers to yield image data defining an image.

22. An ultrasound machine according to claim 21, wherein the ultrasound machine is a portable ultrasound machine having a mass not exceeding 4 ½ kilograms.

23. An ultrasound machine according to claim 21, wherein a number of the plurality of transducer elements exceeds a number of beamformer channels in each of the beamformers.

24. An ultrasound machine according to claim 21, wherein there are at least four of the beamformers.

25. An ultrasound machine according to claim 21, wherein the beamformer is configured to apply weights to the echo signals before summing the echo signals, the weights being distributed from the beamforming coefficient generator to the beamformers by way of the beamformer coefficient bus.

26. An ultrasound machine according to claim 25, wherein the distributing of the delay values and the weights to all of the beamformers is completed in a focal update cycle having a duration of 10 microseconds or less.

27. An ultrasound machine according to claim 21, wherein the ultrasound transmitter is configured to transmit a sequence comprising a plurality of ultrasound signals into the volume of interest; and scanline values derived from echo signals of different ones of the plurality of transmitted ultrasound signals are combined to yield the image.

28. An ultrasound machine according to claim 27, wherein the plurality of beamformers each comprise a plurality of channels, and wherein:
   for a first one of the transmit signals, the ultrasound transmitter is configured to deliver a first subset of the received echo signals corresponding to a first aperture to the channels of the beamformers; and
   for a second one of the transmit signals, the ultrasound transmitter is configured to deliver a second subset of the received echo signals different from the first subset and corresponding to a second aperture to the channels of the beamformers.

29. An ultrasound machine according to claim 27 wherein a first one of the transmit signals comprises a first ultrasound pulse having a first amplitude and a second one of the transmit signals comprises a second ultrasound pulse having a second amplitude equal to the first amplitude and a phase that is inverted relative to the first pulse.

30. An ultrasound machine according to claim 27 wherein the plurality of beamformers each comprise a plurality of channels, and wherein:
   a first set comprising two or more of the transmit signals each comprise a first ultrasound pulse having a first amplitude and a first subset of the received echo signals corresponding to a first aperture is delivered to the channels of the beamformers for a first one of the first set of transmit signals and a second subset of the received echo signals different from the first subset and corresponding to a second aperture is delivered to the channels of the beamformers for a second one of the first set of transmit signals, and
   a second set comprising two or more other ones of the transmit signals each transmit a second ultrasound pulse having the first amplitude and a phase inverted relative to the first pulse and a third subset of the received echo signals corresponding to a third aperture is delivered to the channels of the beamformers for a first one of the second set of transmit signals and a fourth subset of the received echo signals different from the third subset and corresponding to a fourth aperture is delivered to the channels of the beamformers for a second one of the second set of transmit signals.

31. An ultrasound machine according to claim 21, wherein the ultrasound machine further comprises variable-length first-in, first-out (FIFO) registers, and wherein when applying the selected delays to the echo signals, the ultrasound machine is further configured to pass the echo signals through the FIFO registers.

32. An ultrasound machine according to claim 31, wherein when applying the selected delays, the ultrasound machine is further configured to interpolate values of successive samples.

* * * * *